(12) United States Patent
Hasegawa et al.

(10) Patent No.: US 9,230,065 B2
(45) Date of Patent: Jan. 5, 2016

(54) INTENTION CONVEYANCE SUPPORT DEVICE AND METHOD

(75) Inventors: Ryohei Hasegawa, Ibaraki (JP); Yukako Hasegawa, Ibaraki (JP); Hideaki Takai, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 260 days.

(21) Appl. No.: 13/819,901

(22) PCT Filed: Aug. 30, 2011

(86) PCT No.: PCT/JP2011/069524
§ 371 (c)(1),
(2), (4) Date: Feb. 28, 2013

(87) PCT Pub. No.: WO2012/029742
PCT Pub. Date: Mar. 8, 2012

(65) Prior Publication Data
US 2013/0158883 A1 Jun. 20, 2013

(30) Foreign Application Priority Data
Sep. 1, 2010 (JP) ................................. 2010-195463

(51) Int. Cl.
*G06F 19/00* (2011.01)
*A61B 5/0476* (2006.01)
(Continued)

(52) U.S. Cl.
CPC .............. *G06F 19/36* (2013.01); *A61B 5/0476* (2013.01); *A61B 5/0482* (2013.01);
(Continued)

(58) Field of Classification Search
CPC ...... A61B 5/0476; A61B 5/16; A61B 5/7264; A61B 5/0482; A61B 5/04842; G06F 3/015; G06F 19/36; G06K 9/00563
See application file for complete search history.

(56) References Cited

U.S. PATENT DOCUMENTS

| | | | | |
|---|---|---|---|---|
| 5,638,826 A | * | 6/1997 | Wolpaw et al. | 600/544 |
| 2003/0229291 A1 | * | 12/2003 | Collura | 600/545 |

(Continued)

FOREIGN PATENT DOCUMENTS

| | | |
|---|---|---|
| JP | 10080409 | 3/1998 |
| JP | 2009268826 | 11/2009 |
| WO | WO2006051709 | 5/2006 |

OTHER PUBLICATIONS

Calculation of the Decision-Making Process Based on the Act of Monkey Superior Colliculus Neuron; Rhouhei Hasegawa; pp. 32-51 (2007) (with partial translation).

*Primary Examiner* — Christine H Matthews
*Assistant Examiner* — Joshua D Lannu
(74) *Attorney, Agent, or Firm* — McCarter & English

(57) ABSTRACT

According to a conventional BMI technology for controlling external equipment or transmitting an intention to another person by focusing on a biosignal such as brain activity, there has been the problem that a large-sized apparatus is required, the operation method is complex from the user's viewpoint, and noise is large. The present invention provides an apparatus and method such that an intention in the brain can be analyzed with high accuracy and at high speed and transmitted in real-time. A communication assist apparatus according to the present invention comprises an apparatus for presenting a visual stimulus on a display screen and the like, and a processing apparatus for processing brain wave data from an electroencephalograph that measures a brain wave after stimulus presentation by the presenting apparatus. The processing apparatus determines that a specific intention decision has been made in the brain when the product of an accumulated discrimination score according to a discriminant analysis function obtained by analyzing the brain wave data and a success rate exceeds a threshold value, and then outputs a determination result to a device.

4 Claims, 8 Drawing Sheets

(51) Int. Cl.
- *A61B 5/16* (2006.01)
- *G06F 3/01* (2006.01)
- *A61B 5/00* (2006.01)
- *A61B 5/0482* (2006.01)
- *A61B 5/0484* (2006.01)
- *G06K 9/00* (2006.01)

(52) U.S. Cl.
CPC ............. *A61B 5/04842* (2013.01); *A61B 5/16* (2013.01); *A61B 5/7264* (2013.01); *G06F 3/015* (2013.01); *G06K 9/00563* (2013.01)

(56) References Cited

U.S. PATENT DOCUMENTS

| | | | |
|---|---|---|---|
| 2007/0010754 A1* | 1/2007 | Muller et al. | 600/544 |
| 2007/0266273 A1 | 11/2007 | Adachi et al. | |
| 2009/0221928 A1* | 9/2009 | Einav et al. | 600/544 |

* cited by examiner

FIG. 8

| Sample | | | Group |
|---|---|---|---|
| Game | Block | Alternatives (A-H) | |
| 1 | 1 | D | Second group |
| | | B | |
| | | G | |
| | | A | First group |
| | | E | Second group |
| | | ⋮ | |
| | | H | |
| | 2 | E | Second group |
| | | A | First group |
| | | B | Second group |
| | | ⋮ | |
| | | F | |
| | ⋮ | ⋮ | ⋮ |
| | $B_n$ | | |
| 2 | 1 | G | Second group |
| | | A | |
| | | B | First group |
| | | H | Second group |
| | | ⋮ | |
| | ⋮ | ⋮ | ⋮ |
| | $B_n$ | | |
| ⋮ | | | |
| 8 | 1 | | |
| | ⋮ | | |
| | $B_n$ | | |

FIG. 9

| | Explanatory variable (Feature quantity): $x_i$ ($N = tn \times Ch_n$) | | | | | | | | | | |
|---|---|---|---|---|---|---|---|---|---|---|---|
| Channel | 1 | | | | 2 | | | ... | $Ch_n$ | | |
| Sampling number | 1 | 2 | ... | tn | 1 | 2 | ... | tn | 1 | 2 | ... | tn |
| Explanatory variable | $x_1$ | $x_2$ | ... | $x_{tn}$ | $x_{tn+1}$ | | ... | | | | | $x_N$ |

INTENTION CONVEYANCE SUPPORT DEVICE AND METHOD

CROSS REFERENCE TO RELATED APPLICATIONS

This application is a national stage application filed under 35 USC 371 of PCT/JP2011/069524, filed Aug. 30, 2011, which claims the benefit of Japanese Patent Application No. 2010-195463, filed Sep. 1, 2010, all of which are incorporated herein by reference in their entirety.

FIELD OF THE INVENTION

The present invention relates to a communication apparatus and method for detecting brain activity, analyzing an intention of an operator, and transmitting the intention so as to enable direct operation of a device in accordance with the intention of the operator without using his or her hands or legs.

BACKGROUND OF THE INVENTION

Currently, in the fields of information science, medical engineering applications, and welfare device control by brain activity, operation of a device is mainly performed through an input operation of various switches, a joystick, a mouse and the like by hand. Meanwhile, in the field of nursing care/welfare device development, a need is felt for a device that can be operated by other parts of the body for operators with physically disabled hands or legs.

Conventionally, speech assisting devices using a character board or picture cards are known. Technologies related to devices for assisting the conversation of users with disabilities in language function or hearing are discussed in Patent Documents 1 and 2, for example. Patent Document 1 describes a technology such that the letters of the 50 Japanese syllabary on a character board are sequentially lighted on a block by block basis and selected, and a technology involving the use of a message board for selecting a request for bodily care. Patent Document 2 describes a communication assist system for selecting a symbol display by using a portable information terminal. However, in the field of nursing care/welfare device development, a device that enables the direct transmission of an intention without requiring the conventional operations is desired for operators who cannot perform complex input operations, such as the elderly or the sick. There is also a need for a device for patients with speech impediment or the elderly that enables the transmission of an intention regarding basic personal nursing care or feelings, to the helper in a simpler manner.

The progress in brain science in recent years has led to various studies on the relationship between human thought and behavior and brain activity. Attention is being focused on Brain-Machine Interface (BMI) technology for controlling an external device or conveying an intention to others by noting a biosignal, such as brain activity.

For example, neuromarketing is the study for investigating the brain activity related to consumer behavior by using a functional MRI (fMRI) device and the like. A study is known in which, through a brain activity measurement experiment using a fMRI apparatus, brain regions associated with preferences or brand awareness for Coca cola and Pepsi cola were identified and brain activity differences were investigated (Non-patent Document 1).

The present inventors have shown, through a measurement technique involving extracellular recording of the action potential of a single neuron by electrodes disposed in an animal brain, and by a neuronal ensemble activity simulation, that the representation of relationships among a plurality of external stimuli (experimental conditions) in the brain can be estimated in terms of low-dimensional spatial information (see Non-patent Document 2). However, many aspects of brain activity are still unknown, and the measurement methods have restrictions.

The present inventors have also proposed a virtual decision function and shown a calculation method therefor (see Non-patent Document 3). Non-patent Document 3 describes a method for predicting an alternative behavior from a single neuron activity as an example of neural activity.

Patent Document 1: JP-A-2004-286768
Patent Document 2: JP-A-2003-255825
Non-patent Document 1: McClure S M, et al., "Neural Correlates of Behavioral Preference for Culturally Familiar Drinks" Neuron 44, p 379-387, 2004
Non-patent Document 2: N. Matsumoto and R. Hasegawa, "Prediction of Multidimensional Decision-making Based on Single Trial of Frontal Association Area Neuronal Ensemble", Neuroscience Research, Vol. 58, Supplement 1, page S161 (P2-f34), 2007
Non-patent Document 3: R. Hasegawa et al., "Single trial-based prediction of a go/no-go decision in monkey superior colliculus", Neural Networks 19(2006) 1223-1232

There is a need for a device such that an intention can be conveyed to industrial or entertainment devices such as a robot and a wireless control device, or welfare devices such as an electric wheelchair and an electronic character board, without using hands or legs and by as simple an operation as possible. However, the various latest input apparatuses that have been researched and developed for the above purposes require their own unique input systems or input apparatuses. Thus, the various input apparatuses need to be purchased, and it takes time to learn how to operate them.

The technology that examines brain activity by using a functional MRI (fMRI) apparatus and the like requires measurement within the MRI apparatus, so that a real-time input operation cannot be performed and a large-size apparatus is required.

The apparatuses that have been proposed by conventional researches on communication have too much noise for the measurement of biological information such as brain waves, resulting in a low probability of correct answers and a long time before a determination can be made.

The core of the above conventional BMI technologies should be the technology for real-time decoding of an intention decision in the brain. However, it is extremely difficult to decode an intention decision in the brain accurately and quickly under the condition of the on-scalp brain wave recording with poor S/N ratio, or the neuron activity recording with a small number of simultaneously recordable signals. For example, according to a technique, a plurality of alternative visual stimuli is presented on a personal computer screen, and the alternative selected by an operator is predicted or inferred on the basis of the intensity of response of an induced brain wave (an event-related brain wave referred to as "P300", such as a positive potential change 300 milliseconds after the presentation of stimulus) obtained when the stimuli are flashed (lighted) in a pseudo-random manner. In this case, there has been the problem that increasing the number of presentations may increase prediction accuracy but results in longer time, and, conversely, decreasing the number of presentations leads to a decrease in accuracy although the time required for prediction can be decreased.

The present invention aims to overcome the above problems and an object of the present invention is to discriminate an intention in the brain without erroneous identification and in a short time. Another object of the present invention is to enable a device to be directly operated in real-time according to a thought in the brain of an operator. Another object is to provide an apparatus and method such that a patient with speech impediment or the elderly can convey intentions regarding basic personal nursing care or feelings directly and more simply to the helper.

SUMMARY OF THE INVENTION

In order to achieve the foregoing objectives, the present invention employs "a virtual decision function" developed by the present inventors, which is a technique for quantifying the process of intention decision in the brain. The virtual decision function, which is originally an analysis technique for basic research devised for investigating the intention decision mechanism in the brain, has been useful in deducing the process of alternative decision formation that is observed after the elapse of time on the order of milliseconds following the recording of a neuron activity (particular the frequency of firing of an action potential) by electrodes disposed in the brain (see Non-patent Document 3). According to the present invention, the concept of the virtual decision function is greatly expanded and utilized as a technique for decoding an intention in the brain for a communication apparatus based on brain wave measurement. A variable flash control technique such that flashing is terminated and an answer is given when the prediction probability is sufficiently high is also employed.

In order to achieve the foregoing objects, the present invention has the following features.

A communication assist apparatus according to the present invention includes a stimulus-presenting apparatus, and a processing apparatus that processes brain wave data from an electroencephalograph that measures a brain wave after stimulus presentation by the stimulus-presenting apparatus. The processing apparatus determines that a specific intention decision has been made in the brain on the basis of a discriminant function obtained by analyzing the brain wave data and a success rate. When the product of an accumulated discrimination score according to the discriminant function obtained by analyzing the brain wave data and the success rate exceeds a threshold value, it may be determined that the specific intention decision has been made in the brain and then a determination result may be outputted to a device.

The function obtained by analyzing the brain wave data and the function based on the success rate are functions for deducing the process (time course) of an intention decision in the brain. Thus, the functions may be referred to as a virtual decision function (VDF). The function obtained by analyzing the data measured by the electroencephalograph is a multivariate analysis function, such as a logistics function or a linear discriminant analysis function. Weighting of variables may be set for each brain wave channel and at intervals of time elapsed after stimulus presentation.

Preferably, according to the present invention, alternative intention decision may be utilized. Preferably, for implementation of a method for transmitting an intention by the communication apparatus, a learning model may be generated on the basis of an instruction signal. By appropriately adjusting the threshold value by prior simulation, a setting such that either prediction accuracy or prediction speed is given priority or a setting such that they are balanced may be selected.

The stimulus-presenting apparatus according to the present invention may include a display screen as a representative example, which may be provided by a computer display means and the like. The apparatus according to the present invention may be applied for a welfare device.

A communication assist method according to the present invention includes determining that a specific intention decision has been made in the brain on the basis of a discriminant function obtained by analyzing data measured by an electroencephalograph and a success rate. It may be determined that a specific intention decision has been made in the brain when the product of an accumulated discrimination score according to the discriminant function obtained by analyzing the data measured by the electroencephalograph and the success rate exceeds a threshold value, and then a determination result may be outputted to a device.

According to the present invention, an industrial or entertainment device, such as a robot and a wireless control device, or a welfare device such as an electric wheelchair and an electronic character board, can be directly operated by an activity in the brain. According to the present invention, an operator is asked to make an alternative selection, and corresponding biological information such as a brain wave is acquired as a function, whereby operation input information can be acquired with high accuracy, in a short time, and in real-time.

Further, according to the present invention, the operator only needs to be attached with electrodes for measuring the brain wave, as if the operator is wearing a net or a cap provided with the electrodes. By connecting the electrodes and an input apparatus wirelessly, the degree of positional freedom of the operator can be increased such that a decrease in size can be achieved. The present invention does not require the learning of special input operations for transmission of intention, so that a patient with speech impediment or the elderly can convey an intention regarding basic personal nursing care or a feeling to the helper in a simpler and more direct way.

It has been reported that by a conventional technique focusing on blood flow change according to NIRS, decoding of an intention decision in the brain generally takes several tens of seconds. According to the present invention, however, it has been confirmed that prediction accuracy of 90% or more can be achieved within 2 to 3 seconds per selection. According to the present invention, data acquisition can be terminated and a correct answer can be derived at the stage where highly reliable inference can be drawn, without having to wait for completion of a preset number of blocks, as is conventionally required. Thus, high-speed and highly efficient discrimination can be made. In addition, by using the accumulated discrimination score which is obtained by accumulating the discrimination score according to the discriminant function obtained by analyzing brain wave data, the discrimination score is accumulated as the number of blocks is increased. Accordingly, a specific alternative acquires a higher accumulated discrimination score than the other alternatives, so that an inference can be drawn with even higher accuracy and at higher speed and real-time communication can be achieved.

One of a plurality of alternatives may be selected on the basis of a combination of alternative selections. Thus, messages may be displayed in a hierarchical manner, and communication may be implemented by only a few selection operations on the various messages. Accordingly, the present invention enables a message to be conveyed quickly through a simple input operation.

BRIEF DESCRIPTION OF DRAWINGS

FIG. 8 illustrates a data structure according to the second embodiment.

FIG. 9 illustrates data according to the second embodiment.

DETAILED DESCRIPTION OF THE INVENTION

An apparatus and method according to the present invention will be described with reference to embodiments.

The configuration of an embodiment of the present invention mainly includes the following elements.
(1) As a situation for decoding an intention decision in the brain, a behavior task of selecting one of a plurality of visually displayed alternatives (such as visual stimuli) is set.
(2) In each trial of the task, attention is focused on a biosignal that is time-locked to an event, such as a brain activity (e.g., a visually induced P300 brain wave) involved in an intention decision induced immediately after a visual stimulus is presented.
(3) In a model learning data acquisition session (which may be referred to as a "training session"), visually induced brain wave patterns are compared before and after the stimulus presentation and depending on the type of stimulus (such as the difference in alternatives), and an identification model parameter is set at intervals of elapsed time of stimulus presentation.
(4) In a behavior prediction session (which may also be referred to as a "test session"), the value of a discriminant analysis function obtained by using the determined parameter is multiplied with a determination coefficient (a coefficient indicating probability, such as a success rate) on millisecond time basis, whereby what decision is represented with what probability in the brain can be deduced in terms of continuous value changes. The function for deducing the process of such intention decision in the brain (time course) is referred to as a virtual decision function (VDF).
(5) When the virtual decision function exceeds a threshold value, it is determined that a specific intention decision has been made in the brain, and the determination result is transmitted to an external process.

According to the present invention, alternative intention decision is made. In the case of alternative decision, an intention decision can be exclusively deduced by allocating a higher VDF value to one alternative and a lower value to the other alternative, with zero at the center. By combining a plurality of VDFs (a plurality of alternatives), it is possible to assume power-of-two multidimensional decisions. It is also possible to alternatively evaluate whether each alternative should be selected and adopt an alternative that has exceeded the threshold value earliest.

As to the threshold value, the threshold value may be appropriately adjusted by prior simulation so that a setting in which priority is given to either prediction accuracy or prediction speed, or a setting in which both are balanced, can be selected.

According to the present invention, upon determination that a specific intention decision has been made in the brain, the determination result is transmitted to the external equipment, whereby a system for controlling a welfare device or transmitting an intention to others in real-time can be constructed.

First Embodiment

Figure 1:
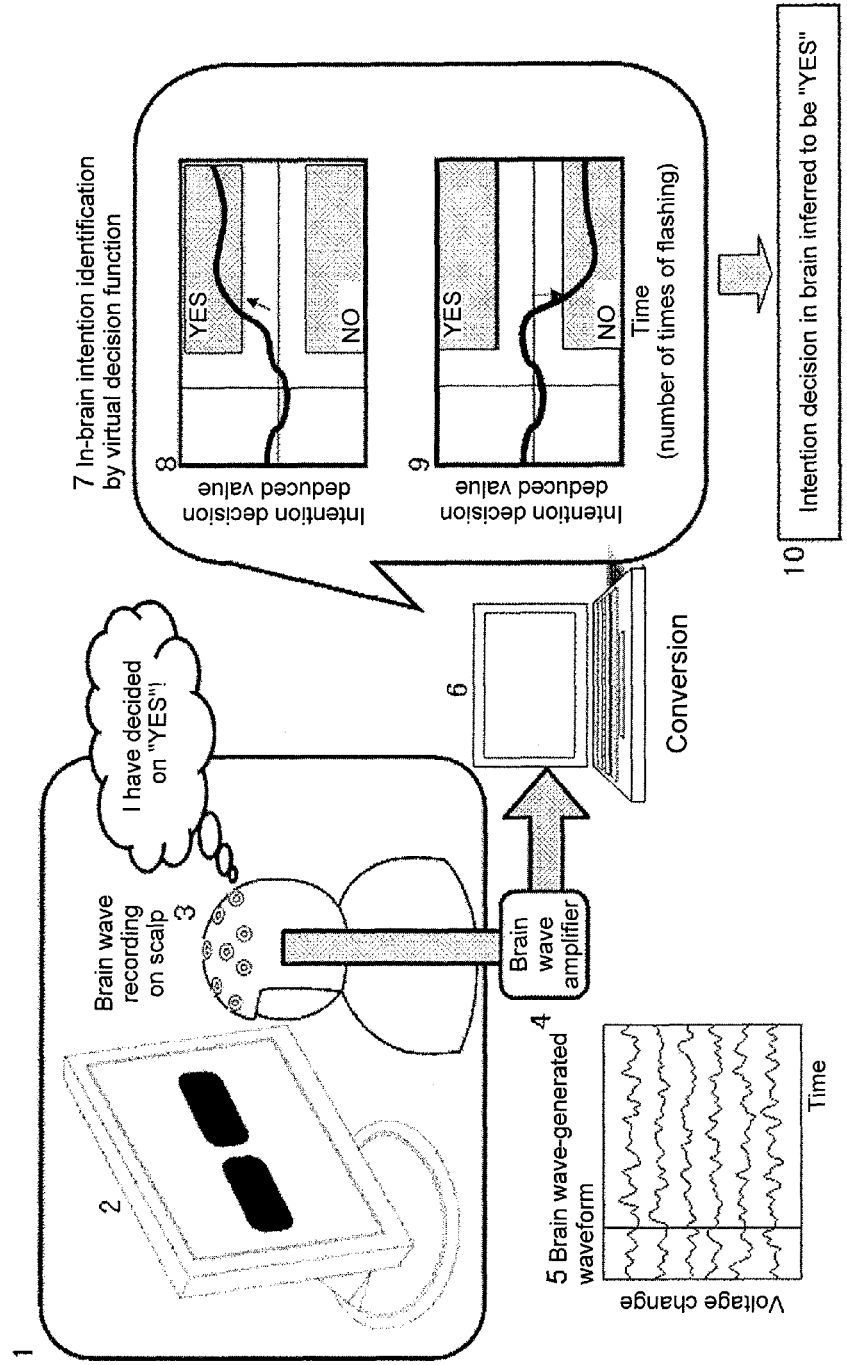
FIG. 1 schematically illustrates an input apparatus and method according to a first embodiment.
Figure 2:
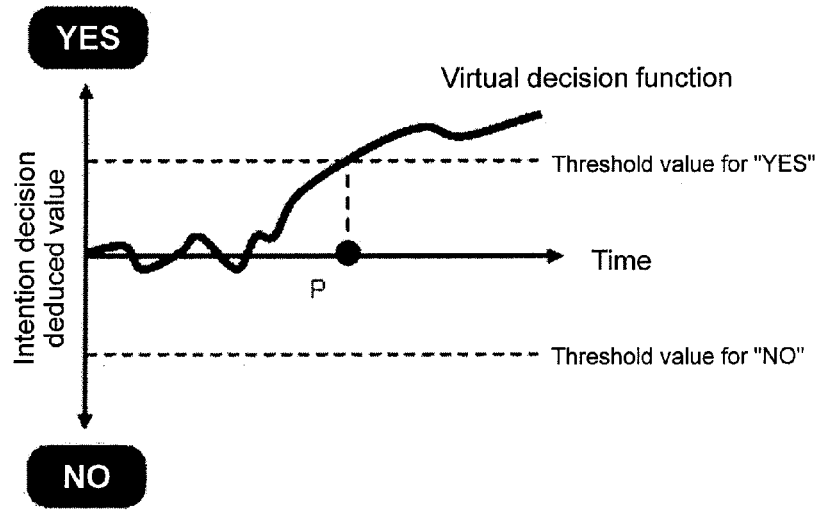
FIG. 2 illustrates the identification of an intention in the brain by a virtual decision function according to the first embodiment.

An embodiment will be described with reference to FIG. 1. FIG. 1 schematically illustrates a communication assist apparatus and method according to the present embodiment. FIG. 2 illustrates in-brain intention identification 7 by the virtual decision function illustrated in FIG. 1.

A test subject is shown a display screen 2 for stimulus presentation, and a brain wave in the scalp of the test subject is recorded (see stimulus presentation 1 to the test subject in FIG. 1). The test subject for the implementation may include a general device user, a non-handicapped person, a handicapped person requiring nursing care, or the elderly. The test subject wears a brain wave measuring electrode 3 on the head for measuring brain waves. For example, a head cap with fixed brain wave measuring electrodes is used. On the display screen (monitor), various visual stimuli are presented. The test subject is given a task of making a decision "Yes" or "No" in response to the presented visual stimuli. For example, the test subject is shown the screen flashing "Yes" and "No" alternately, while his or her brain activity is measured by an electroencephalograph (a brain wave amplifier 4 in the figure). For example, data illustrated as brain wave raw waveforms 5 (the horizontal axis showing elapsed time since stimulus and the vertical axis showing voltage change) are obtained. The brain wave raw waveform data are analyzed by a computer 6, the virtual decision function is calculated, and the intention decision by the test subject is predicted (see in-brain intention identification 7 by the virtual decision function illustrated in FIG. 1). In the process of the in-brain intention identification 7 by the virtual decision function, when the virtual decision function immediately after the flashing of "Yes" is in the region "Yes" of an intention decision deduced value (8), it is inferred that the intention decision in the brain is "Yes" (10). On the other hand, when the virtual decision function immediately after the flashing of "No" is in the region "No" of the intention decision deduced value (9), it is inferred that the intention decision in the brain is "No". In the graphs for the in-brain intention identification 7 by the virtual decision function illustrated in FIG. 1, the horizontal axis shows the number of times of alternate flashing of "Yes" and "No", and the vertical axis shows the value of the virtual decision function, or the "intention decision deduced value". The region "Yes" of the intention decision deduced value is a region where the virtual decision function is not less than a predetermined threshold value. The region "No" of the intention decision deduced value is a region where the virtual decision function is not more than a predetermined threshold value. On the horizontal axis, an appropriate number of times of flashing, such as two or more, may correspond to the regions "Yes" and "No" for intention decision deduction. While in the graphs in FIG. 1 for in-brain intention identification by the virtual decision function, the lines represent the total number of times of flashing, the lines are illustrative. Preferably, when a predetermined threshold value is exceeded, it may be determined that a specific intention decision has been made in the brain and flashing may be terminated. In FIG. 2, as in the in-brain intention identification 7 by the virtual decision function illustrated in FIG. 1, the horizontal axis shows the number of times of alternate flashing of "Yes" and "No", and the vertical axis shows the value of the virtual decision function, i.e., the intention decision deduced value. FIG. 2 shows that the virtual decision function exceeded the threshold value for "Yes" at the stimulus elapsed time P.

Whether the predicted result of the above determination is correct may be evaluated in comparison with the expression of the contents of the intention decision orally or by a button. Because the threshold value can be adjusted by prior simulation, the threshold value can be set in accordance with the need for prediction accuracy or prediction speed.

An output signal for the intention decision deduced value may be transmitted to the computer as an input signal for producing a display on a display screen or controlling the operation of a device. Thus, the apparatus according to the present invention, upon identification of an intention decision by the operator on the basis of the biosignal due to a brain wave, can display the result of identification on the screen or perform an operation of an actual machine, for example. Accordingly, the operator can operate a device or transmit an intention via an intuitive interface.

Second Embodiment

While according to the first embodiment a basic example has been described, an electronic message board may be used as the device to be operated. An electronic message board is a communication assist tool for people with severe motor function or speech function impairment. A simple one may allow for the selection of "Yes" or "No"; a more complicated one may enable the selection of various emotions or specific messages regarding the need for relieving oneself or bodily care, by using a keyboard or a touch panel, thus enabling communications with others.

Figure 3:
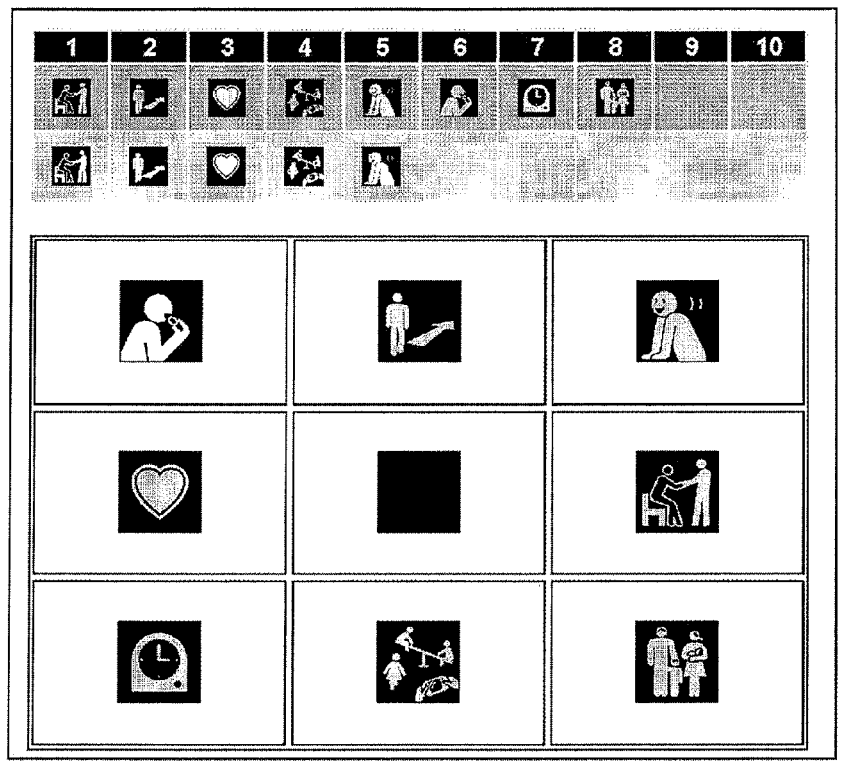
FIG. 3 illustrates a display screen used according to a second embodiment.

According to the second embodiment, an example in which a number of alternatives are displayed on a display screen and one is selected from the many will be described with reference to FIGS. 3 to 9. FIG. 3 illustrates an example of the display screen used according to the present embodiment. On the display screen, a number of symbol displays of pictures or letters are displayed, and the brain wave of the user, particularly an event-related brain wave referred to as "P300" (a positive potential change 300 milliseconds after stimulus presentation) is measured while the locations that are lighted are changed by lighting the symbol displays in order or randomly. Then, the virtual decision function is determined and, when the prediction probability is sufficiently high, flashing is interrupted, and the symbol display that the user wishes to convey (alternative the user wishes to select; a target) is detected as an input. This takes advantage of the phenomenon in which the brain wave becomes stronger at the moment of flashing of the symbol display of interest. According to the present embodiment, LDA (linear discriminant analysis) is utilized.

Figure 4:
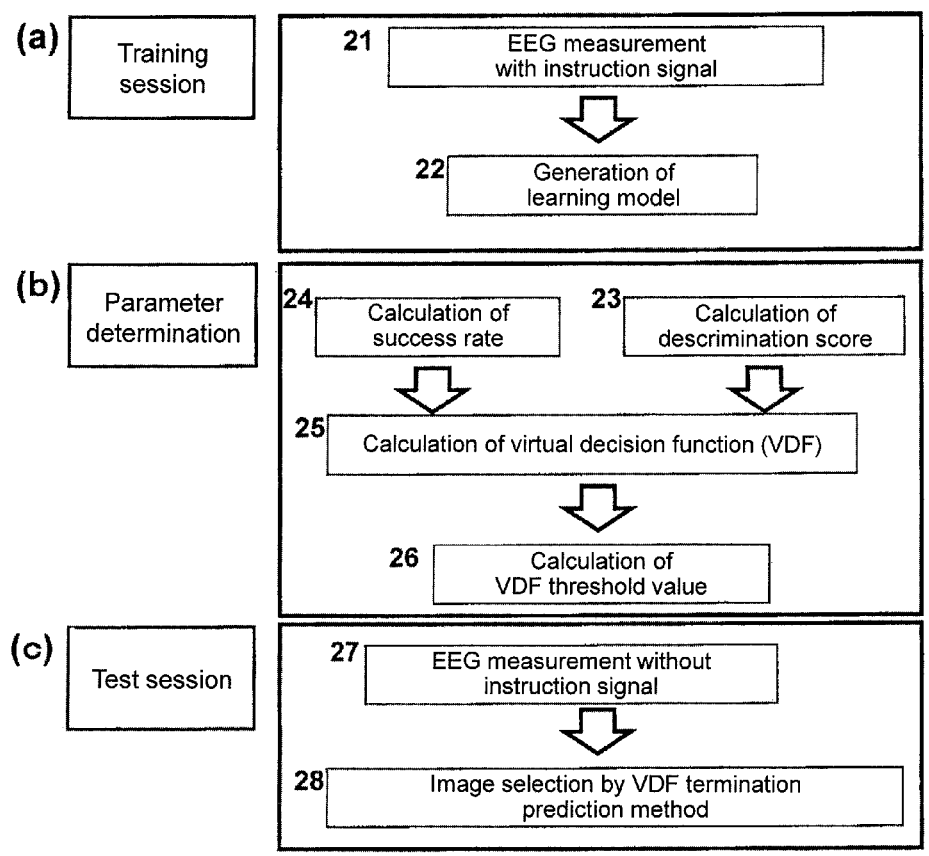
FIG. 4 illustrates a discriminant analysis process according to the second embodiment.

The process of discriminant analysis according to the present embodiment will be described with reference to FIG. 4. Preferably, before implementation, a training session and parameter determination may be performed so as to increase the accuracy of decoding of the intention transmitted by the user prior to actual use, followed by a test session (implementation).

(a) Training Session

Figure 5:
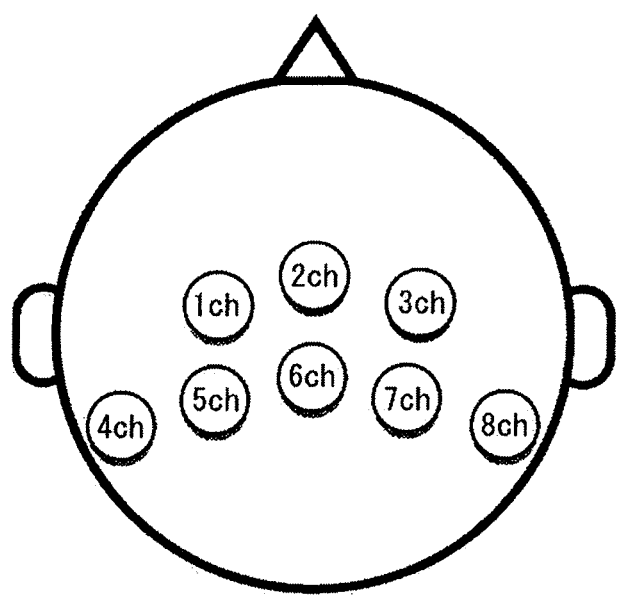
FIG. 5 schematically illustrates an arrangement of brain wave electrodes on the head of a test subject according to the second embodiment.

In a training session (a), EEG (electroencephalograph, the device that measures a potential change on the scalp) measurement 21 is performed together with an instruction signal so as to generate (22) a learning model. For example, as shown in FIG. 1, eight symbol displays (pictograms) are displayed on the display screen and the locations that are flashed (lighted) are cycled through once, thus creating a first block. Similarly, the first through the 15th blocks are successively flashed, while the brain wave of the test subject (channels 1 through 8 corresponding to the position of the electrodes) is measured. FIG. 5 schematically illustrates an arrangement of the brain wave electrodes on the head of the test subject. The test subject is asked to think of one specific symbol display (target) that he or she wishes to convey. Similarly, measurement for the first through the 15th blocks is successively taken. In this way, measurement for the first through the 15th blocks is taken for the eight symbol displays, i.e., for all of the symbol displays.

Figure 6:
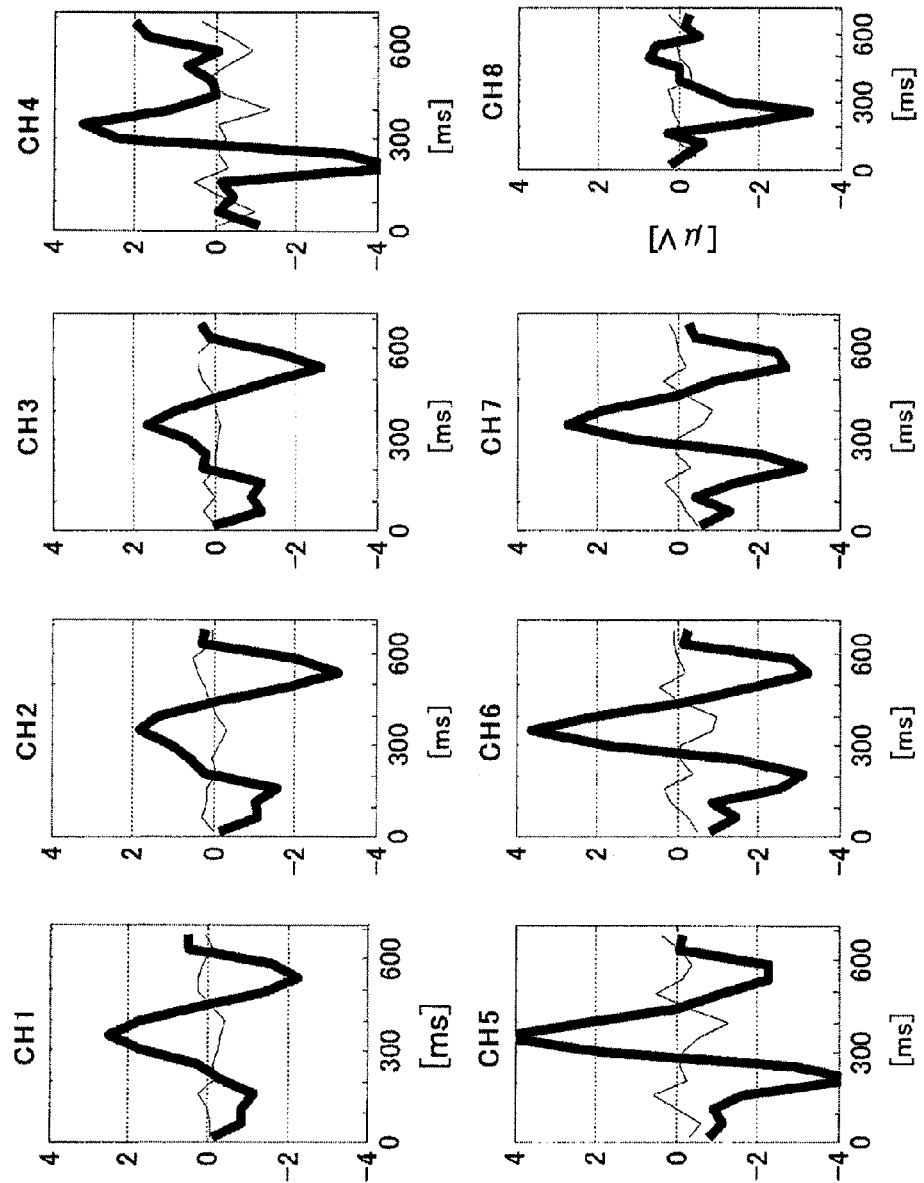
FIG. 6 illustrates brain wave-generated waveforms for all of trials according to the second embodiment.

FIG. 6 illustrates a by-condition comparison of the mean values of brain wave-generated waveforms for all of the trials. FIG. 6 illustrates the P300 induced brain waves for ch1 through ch8 upon presentation of a target stimulus. Recordings are made for all of the channels ch1 through ch8. The bold lines indicate the induced brain waves in response to a picture card of interest (the alternative the test subject wishes to select; target) (answer "Yes"), while the thin lines indicate the induced brain waves in response to a picture card other than the card of interest (non-target) (answer "No"). It will be seen that the difference varies depending on the channel and the elapsed time (ms).

(b) Parameter Determination

After the learning model is generated, calculation 23 of a discrimination score (LDA Score) is conducted. The brain wave potential measured by the electroencephalograph differs between the brain wave in response to the target symbol display (answer "Yes") and the brain wave in response to the non-target symbol display (answer "No"), depending on the channel and the elapsed time after the stimulus. Thus, weighting coefficients for discriminant analysis are determined and set in accordance with the individual channels and the elapsed time after stimulus. By using the weighting coefficients, the discrimination score can be calculated.

On the basis of the results of the calculation 23 of the discrimination score and the calculation 24 of the success rate, calculation 25 of a function (referred to as the "virtual decision function VDF" according to the present invention) that enables the determination of intention in a virtual manner is conducted. Then, calculation 26 of a threshold value for the virtual decision function VDF is conducted, and the threshold value is set.

(c) Test Session (Implementation)

This is a session in which actual communication discrimination is conducted in real-time. EEG measurement 27 is conducted without the instruction signal. When the virtual decision function has reached the threshold value or above, EEG measurement is terminated (image selection 28 by a VDF termination prediction method), it is determined that a decision has been made, and the selected pictogram is transmitted to a device. Alternatively, one of the symbol displays that has the highest VDF value or that has reached the predetermined value first, or a symbol display with a higher VDF value than the other symbol displays may be determined to have been selected and transmitted to the device.

For example, eight symbol displays are displayed on the display screen, as illustrated in FIG. 1, and the locations that are flashed (lighted) are cycled once randomly, producing the first block. Similarly, the second block and the third block are successively flashed while the brain waves (for channels 1 through 8 corresponding to the positions of the electrodes) are measured. When the virtual decision function has reached the threshold value or above, it is determined that the prediction probability is sufficiently high, so that flashing is terminated and the symbol display that the user wishes to convey is detected as an input.

Figure 7:
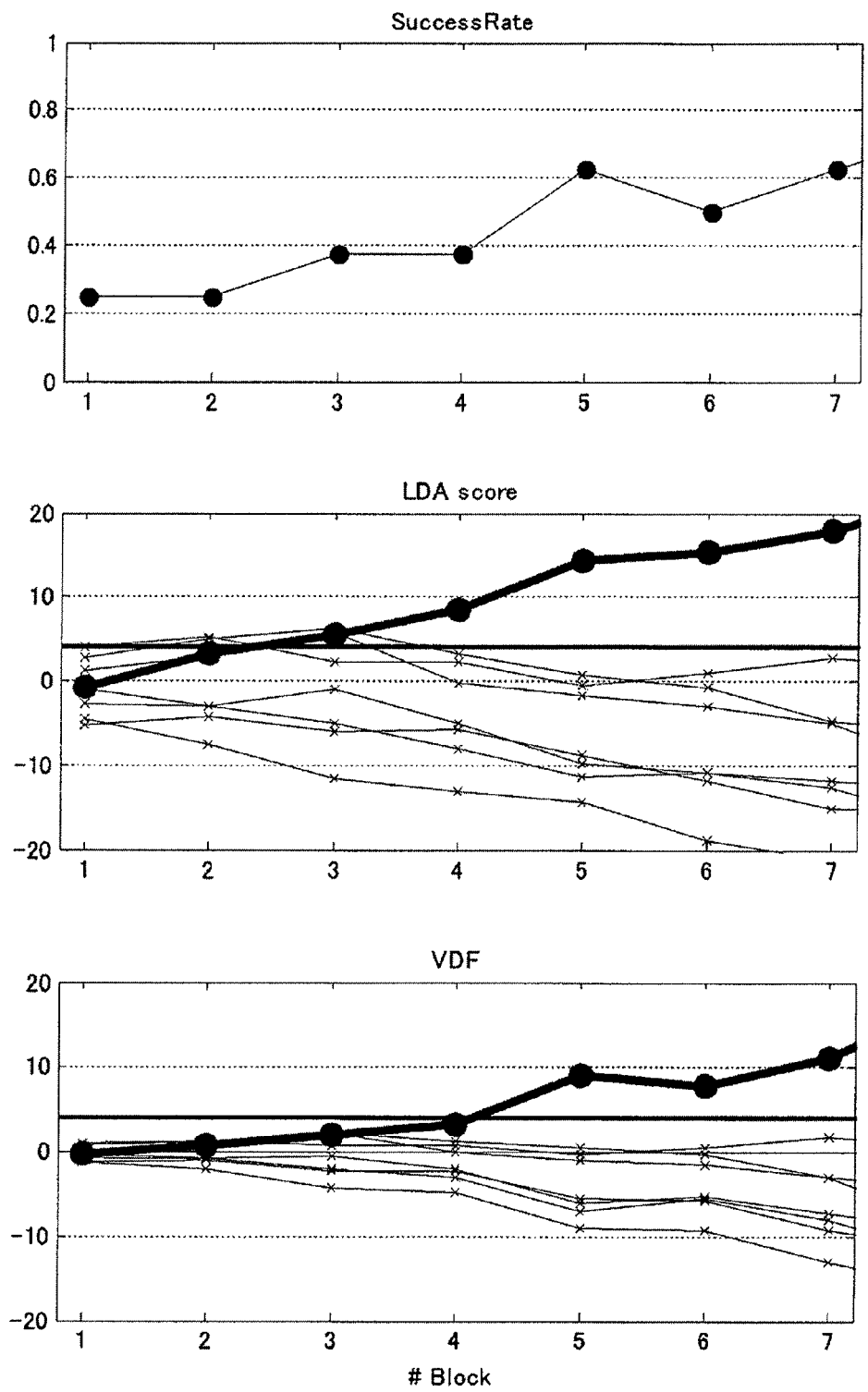
FIG. 7 illustrates the success rate, discrimination score, and VDF according to the second embodiment.

FIG. 7 illustrates an example in which the VDF is calculated in real-time and an answer is given halfway through. In FIG. 7, the top, the middle and the bottom correspond to the success rate, the discrimination score (LDA score), and the VDF, respectively. The polygonal lines in FIG. 7 indicate the values measured when the respective symbol displays are flashed, with the horizontal axis showing the number of times of the blocks. The bottom of FIG. 7 shows that the thick line exceeding the threshold value (thick horizontal line; how the threshold value is set will be described later) at the number of times of block 5. In this example, flashing is terminated at the number of times of block 5, and the symbol display that has reached the threshold value is transmitted as the answer; namely, the symbol display is used as the input operation signal for the predetermined device. In the example of FIG. 7, flashing is performed up to block 7 to demonstrate the comparative time-wise superiority of the present embodiment.

According to the present embodiment, compared with the method by which a single identification is made at the end on the basis of data for a fixed number of times of flashed stimuli, an answer can be obtained fast because the flashing is terminated upon reaching a threshold value. However, it is seen from the figure that a correct decision may not be made if the focus is placed on the discrimination score and a candidate that reaches the same threshold value is to be selected, because the candidate exceeding the threshold value in block 2 that shows the maximum discrimination score may be different from the target candidate. Thus, it has been shown that the termination method focusing on the VDF enables high-speed prediction while high accuracy is maintained.

The present embodiment will be described with reference to the drawings and mathematical expressions.

(A) Data Structure and Classification by Discriminant Function

Stimuli corresponding to eight alternatives (one of eight arranged alternatives is flashed, or one of eight is presented on the screen) are given, each once, in a pseudo-random order (producing a block). One block is the unit of a cycle of the stimulus through the alternatives. For each determination of an alternative (one game), stimulation is repeated for a preset number of blocks ($B_n$) (see FIG. 8). The explanatory variable (feature quantity) $x_i$ for each stimulus is a combination of voltage values (amplitude values) of the brain wave in each of time windows after stimulus that have been recorded in each channel (see FIG. 9). The time windows are the first through the tn-th sampling intervals, the first sampling interval corresponding to the timing of occurrence of stimulus. The sampling intervals correspond to the elapsed time on the horizontal axis of the brain wave-generated waveforms in FIG. 6. For example, n is 15. Thus, the number of $x_i$ is $N=tn \times Ch_n$.

(A-1) In order to determine one of the alternatives that is to be selected, a discriminant function (referred to as a "model") for dividing one of the alternatives into a first group (target) and the others into a second group (non-target) is prepared.

$$y = \sum_{i=1}^{N} a_i x_i + a_0$$

The first group is discriminated when the discrimination score (y value) of the discriminant function is positive, while the second group is discriminated when the discrimination score is negative. When the variable x is standardized, the magnitude of the coefficient a corresponds to the magnitude of the influence of the variable on discrimination.

(A-2) The discrimination scores (y values) for the alternatives are calculated and compared, and the alternative indicating the highest discrimination score is deduced as being the alternative to be selected.

First, in a step of preparing the model, measurements are taken in a plurality of games after it is decided which alternative is the target (for example, in Table 1, "A" is the target for the first game, and "B" is the target for the second game).

(B) How to Determine the Linear Discriminant Function y

While there are various types of the discriminant function, a linear discriminant function will be described in the following. This discriminant expression is drawn at a position farthest from the two groups such that the best reference line for dividing the two groups can be provided. In this case, the coefficient a is determined by maximizing the ratio of the between-class variation (variation between the groups) to the total variation (variation of the two groups as a whole). For this, a method that utilizes variance and covariance may be used, as will be described below.

(B-1) For each of the first group and the second group, the variance (sum of squares) $S_{ii}$ between samples k for each variable and the between-sample covariance (sum of products) $S_{ij}$ between the variables are determined.

$$S_{ii} = \sum_k (x_i(k) - \bar{x}_i)^2,$$

$$S_{ij} = \sum_k (x_i(k) - \bar{x}_i)(x_j(k) - \bar{x}_j)$$

where $\bar{x}_i$ is the between-sample mean of the i-th variable x.

(B-2) The sum of squares and the sum of products of the first group and the second group are pooled by summing for the same two variables and dividing by the degree of freedom $N1+N2-2$.

$$S_{ij} = (S_{ij}(\text{first group}) + S_{ij}(\text{second group}))/(N1+N2-2)$$

where N1 and N2 are the numbers of samples for the first group and the second group, respectively. In the case of FIG. 8, for example, N1 and N2 are the number of games×the number of blocks×the number of target alternatives and the number of games×the number of blocks×the number of non-target alternatives, respectively.

(B-3) Let $S_{ij}$ be a variance-covariance matrix S with corresponding i rows and j columns, and let a matrix in which the coefficients a for the respective variables are arranged in n rows and one column be A, and a matrix in which the mean values of the variables for the first group from which the mean value of the variables for the second group has been subtracted, i.e., $x_i$ (first group)−$x_i$ (second group), are arranged in n rows and one column be X, then the following is valid:

$$SA=X, \text{ therefore } A=S^{-1}X$$

(B-4) Thus, the coefficient a for each variable can be determined. The constant term is $a_0=-\frac{1}{2}[a_1 \{x_1(\text{first group mean value})+x_1(\text{second group mean value})\}+\ldots+a_n\{x_n(\text{first group mean value})+x_n(\text{second group mean value})\}]$.

(C) How to Determine success Rate by Discrimination Score

In a conventional brain wave identification method using discriminant analysis, a fixed number of blocks of data are acquired, a discriminant analysis is performed only once, and the alternative that shows the highest discrimination score value is deduced as the "correct answer". However, in this fixed number-of-times method, the percentage of correct answers (which may also be referred to as "success rate") may be lowered if the number of blocks is too small although the data acquisition time may be decreased. Conversely, if the number of blocks is too large, the data acquisition time may be unnecessarily extended although the percentage of correct answers may be increased. Thus, in order to examine how accurate discriminant analysis can be performed with reference to how many blocks, the relationship between the number of times of stimulus presentation (number of blocks) and the success rate by discriminant analysis is determined. A specific procedure will be described in the following.

(C-1) For each game, the discrimination score y(b) for each alternative in block b is determined according to the expression of (A-1) as each block elapses, and the accumulated discrimination score Y(b) accumulated so far is calculated.

$$y(b) = \sum_i a_i x_i(b) + a_0$$

$$Y(b) = \sum_{k=1}^{b} y(k) = ba_0 + \sum_{k=1}^{b} \sum_i a_i x_i(k)$$

A data discrimination score is obtained by cross-validation. Namely, a discriminant expression is obtained by taking the data for a game out of the original data, and then it is verified whether a valid result can be obtained when the data for the game that has been taken out is applied as new data, repeatedly for all of the games.

(C-2) In each block, one of the alternatives that has the highest accumulated discrimination score Y (the alternative that the user has the intention of selecting at the moment) is determined as an output.

(C-3) This is performed for all of the games, and the success rate SR (the ratio of the number of games with outputs corresponding to the target) for each block is obtained by examining whether the output corresponds to the predetermined target.

(D) How to determine virtual decision function (VDF) by using discrimination score and success rate.

Normally, as the number of blocks is increased and the discrimination score is accumulated, a specific alternative acquires a high accumulated discrimination score compared with the other alternatives. In this case, if data acquisition can be terminated and the correct answer can be derived at the stage where highly reliable inference can be made without waiting for the end of the preset number of blocks, as is done conventionally, highly efficient discrimination can be made. According to the present invention, in order to deduce the intention decision in the brain at high speed and with high accuracy by such a "termination method", a candidate that has reached a threshold value earliest is deduced to be the candidate to be selected, as will be described below. However, the threshold value needs to be set in view of the variation in the discrimination score due to the data for a block of a number of times with relatively low reliability (i.e., the probability of reaching the threshold value by chance). According to the present invention, the concept of virtual decision function according to Non-patent Document 3 is significantly extended and utilized as a technique for decoding an intention in the brain for a communication apparatus based on brain wave measurement, in accordance with a procedure described below.

(D-1) The accumulated discrimination score Y obtained in (C-1) is multiplied with the success rate for the block obtained in (C-3) to obtain the virtual decision function VDF.

$$VDF(b) = SR(b) \cdot Y(b)$$

(E) How to Determine Threshold Value (E-1) The number of blocks and the corresponding output when the VDF of any of the candidates in each game has exceeded an arbitrary value (threshold value candidate) for the first time are obtained, and the success rate and the average number of blocks for each threshold value candidate are determined.

(E-2) One of the threshold value candidates with the highest success rate that has the least average number of blocks is determined as the threshold value $\theta$.

(F) Termination technique using VDF and threshold value.

By using the values of a, SR, and $\theta$ obtained by the techniques (A) to (E), a new game is performed. It should be noted that the value of a is obtained on the basis of the data of all of the games measured for model preparation.

(F-1) The VDF for each alternative is determined as each block elapses.

(F-2) When the VDF value for an alternative has exceeded the threshold value $\theta$, the output is determined at the point in time of the particular block and the processing for the game is completed without performing the subsequent blocks.

According to (A) to (F), the intention in the brain can be decoded in real-time and the transmission of the intention can be assisted. While the description using mathematical expressions has been made with reference to the accumulated discrimination score, the embodiment may be implemented similarly by using a non-accumulated discrimination score.

With regard to the setting of the threshold value, the relationship between the threshold value and the success rate is such that the success rate is increased as the threshold value is increased, whereas the success rate is decreased as the threshold value is decreased. While the number of times of the blocks reached may be decreased by decreasing the set value for the threshold value, noise is increased, resulting in a decrease in discrimination accuracy. The threshold value may be appropriately selected in accordance with the desired accuracy and speed of transmission of intention.

By adapting the symbol displays that are presented according to the foregoing embodiment such that constituent elements for a conversation are hierarchically displayed, for example, a complex intention can be conveyed by displaying a plurality of the symbol displays in the selection screen for each layer and combining the constituent elements selected in the respective layers. For example, various messages can be generated by only a few selection operations. Specifically, according to the present invention, one of 512 kinds of messages can be selected through a simple input operation of selecting one of eight kinds of alternatives three times. Thus, the present invention can be utilized even by a user with insufficient speech skill and insufficient functionality for delicate hand movements, for example.

While the embodiments have been described with reference to a visual stimulus, a hearing stimulus and the like may be given instead, and the corresponding brain wave may be measured and analyzed.

The examples indicated according to the foregoing embodiments and the like are intended to aid the reader in understanding the invention, which is not limited to the embodiments.

INDUSTRIAL APPLICABILITY

According to the present invention, an intention in the brain can be decoded in real-time without using hands or legs and the like. Thus, the present invention can be utilized as a communication assist apparatus or an input assisting means for a general user input apparatus.

REFERENCE SIGNS LIST

1: Presentation of stimulus to test subject
2: Display screen
3: Electrodes for measuring brain wave of test subject
4: Brain wave amplifier
5: Brain wave-generated waveform
6: Computer
7: In-brain intention identification
8: Intention decision in the brain "Yes"
9: Intention decision in the brain "No"
10: Result of determination of intention decision in the brain

The invention claimed is:

1. A communication assist method, comprising:
   obtaining brain wave data from an electroencephalograph;
   analyzing the brain wave data;
   determining a discriminant function based on the analyzed brain wave data;
   determining a success rate based on the discriminant function;
   determining that a specific intention decision has been made in the brain when a product of an accumulated discrimination score according to the discriminant function and the success rate exceeds a threshold value; and
   outputting a determination result of the specific intention decision to an electronic device;
   wherein the analyzing and determining steps are performed by a communication assist apparatus, the communication assist apparatus comprising:
      a stimulus-presenting apparatus; and
      a processing apparatus that processes the brain wave data from the electroencephalograph that measures a brain wave after stimulus presentation by the stimulus-presenting apparatus.

2. The communication assist method according to claim 1, wherein the discriminant function obtained by analyzing the brain wave data measured by the electroencephalograph is a multivariate analysis function.

3. The communication assist method according to claim 1, wherein a weighting of variables is set for each of a plurality of brain wave channels, and wherein the weighting of variables is set at intervals of time elapsed after the stimulus presentation by the stimulus-presenting apparatus.

4. The communication assist method according to claim 1, further comprising determining an alternative intention decision.

* * * * *